United States Patent [19]

Harding

[11] 4,258,256

[45] Mar. 24, 1981

[54] DEVICE FOR EXAMINING A BODY BY MEANS OF PENETRATING RADIATION

[75] Inventor: Geoffrey Harding, Rellingen, Fed. Rep. of Germany

[73] Assignee: U.S. Philips Corporation, New York, N.Y.

[21] Appl. No.: 971,769

[22] Filed: Dec. 21, 1978

[30] Foreign Application Priority Data

Dec. 22, 1977 [DE] Fed. Rep. of Germany ....... 2757320

[51] Int. Cl.$^3$ .................... G01N 23/20; G21K 1/00
[52] U.S. Cl. .................................. 250/272; 250/508
[58] Field of Search .............. 250/272, 273, 508, 505, 250/358 R

[56] References Cited

U.S. PATENT DOCUMENTS

| | | | |
|---|---|---|---|
| 1,164,987 | 12/1915 | Bucky | 250/508 |
| 4,124,804 | 11/1978 | Mirell | 250/358 R |

Primary Examiner—Alfred E. Smith
Assistant Examiner—Thomas P. O'Hare
Attorney, Agent, or Firm—Thomas A. Briody; Robert T. Mayer; Jack E. Haken

[57] ABSTRACT

A body is irradiated by a primary radiation beam; the scattered radiation produced thereby is incident on a detector device consisting of a plurality of detectors and is a measure for the density distribution of materials in the primary beam. However, this gives rise to multiple scattered radiation which disturbs the measurement. The present invention provides a device in which disturbance by multiple scattered radiation is greatly reduced, without any significant effect on the scattered radiation originating from the primary beam. A device in accordance with the invention is provided with flat laminations which are arranged between the primary beam and the detector device and which are aligned with the primary beam in a fan of flat planes.

4 Claims, 2 Drawing Figures

DEVICE FOR EXAMINING A BODY BY MEANS OF PENETRATING RADIATION

The invention relates to a device for examining a body by means of penetrating radiation, a primary beam of small cross-section area passing through the body and the scattered radiation produced thereby being incident, via a slit aperture, on a detector device consisting of a plurality of detectors. Such a device is diagrammatically shown in FIG. 1. A body 1 to be examined is arranged on a table top 2 and is irradiated by a primary X-ray beam 3 which extends horizontally in the Figure. The X-ray beam is generated and collimated by two radiation sources, comprising aperture devices 4a, 5a and 4b, 5b, which are arranged on both sides of the body. The dimensions of the stopped primary beam determine the resolution of the device. The smaller the diameter of the beam is, the higher the resolution will be.

The voltage applied to the X-ray tube during examination amounts to approximately 350 kV. As a result, on the one hand the patient is exposed to only a small radiation dose, while on the other hand the attenuation of the primary beam by photoabsorption is small in comparison with the attenuation by Compton scattering.

The scattered radiation produced by the primary beam 3 in the irradiated part of the body reaches a detector group D, D' via a slit-like (preferably adjustable) opening 7, 7' in a slit aperture 6, 6' arranged above and underneath the body to be examined. Each of the detector groups is composed of a large number of detectors, denoted by the references $d_1$, $d_2$, $d_3$ for the detector D, which are adjacently arranged in a straight line which extends parallel to the primary beam. The surface of the detectors which acts as a measuring surface is shaped as an elongate rectangle, the long sides of which extend parallel to the long sides of the slit-like opening 7, 7'. The slit-like opening 7, 7' of the slit aperture 6, 6', has dimensions which are smaller than the detectors in both directions (i.e. in the longitudinal direction and in the direction of the primary beam) by the same ratio as their distance from the primary beam.

The detectors may be, for example, chambers which are filled with a pressurized rare gas (xenon) which absorbs the radiation and in which two parallel electrodes are arranged which intercept charge carriers ionized by the scattered radiation. Detectors of this kind are described, for example, in German Offenlegungsschrift No. 26 24 448.

The slit aperture ensures an unambiguous relationship between a point on the primary beam and a detector of the detector group D, D'. As is shown in the drawing, for example, the scattered radiation cone 9' produced by the primary beam in a given point is incident on the detector device d' along a given strip which is associated with a detector or with two adjoining detectors. Thus, each detector detects the scattered radiation originating from a given point or region of the primary beam, each point or region of the primary beam being associated with a different detector.

By relative displacement between the body 1 and the primary radiation beam 3 passing therethrough, subsequently different regions of the body can be irradiated and the density distribution thereof can be measured by means of the detector device D, D'. By repeating this operation for a large number of positions, the density distribution in an arbitrary plane of the body can thus be measured. This plane need not necessarily be a flat plane.

Even though the scattered radiation is used for measuring the density distributions on the one hand, the measuring results measured by means of the detector device D, D' are disturbed by scattered radiation on the other hand. Part of the scattered radiation produced in the body at the area of the primary beam is scattered again, or even a number of times, in the body, so that via the slit 7, 7' it is incident on a different detector than the one on which the scattered radiation from the point of origin of the multiply scattered radiation is directly incident.

In order to eliminate the disturbing of the measuring results by the multiple scattering, the use of radiation sources with mainly mono-energetic radiation has been proposed to take into account, for each detector, only the part of the incident scattered radiation whose wavelength has a value to be anticipated considering the wavelength of the primary radiation and the given scattering angle. For this purpose crystal detectors and amplitude discriminators connected thereto are required; in that case, it is not possible to use X-ray tubes as the radiation sources, because such tubes are not capable of generating mono-energetic radiation in the desired energy range.

In order to correct the errors caused by the multiple scattered radiation, it was proposed to subtract the mean value of the output signals of additional detectors from the detector output signals, said additional detectors being arranged so that they are not exposed to the scattered radiation produced in the primary beam 3, but rather to the radiation formed by the multiple scattering in other areas of the body. This solution is also comparatively complex.

To this end, the present invention has for its object to provide a device for examining a body by means of penetrating radiation which comprises simple means for mitigating the disturbing effect of the multiple scattered radiation.

In accordance with the invention, a device of the kind set forth is characterized in that a large number of laminations of a material having a high absorption factor for the radiation are arranged in a region between the primary beam and the detector device so that the radiation generated at the area of the primary beam is not substantially attenuated by the laminations, while the radiation originating from the region outside the primary beam is greatly absorbed.

It is easiest to manufacture flat laminations which extend parallel with respect to each other. However, at the edges of the detector device such laminations would absorb the scattered radiation originating from the region of the primary beam compartively strongly and transmit a comparatively large part of the multiple scattered radiation originating from the region outside the primary beam. In a further embodiment in accordance with the invention, the laminations are arranged so that the prolongation of each lamination at least approximately intersects the primary beam along its entire length.

Although other shapes of the laminations can, in principle, also be used, the manufacture is particularly simple when the laminations are flat and are arranged in flat planes which have a common, straight line of intersection which at least approximately coincides with the primary beam.

In an optimum embodiment in accordance with the invention, the distance S of the laminations on the side facing the primary beam is given by the relation $S=wL/L_p$, in which w is the diameter of a cross section through the primary beam, $L_p$ the distance between the primary beam and the detector device, and L the distance from the side of the laminations facing the primary beam to the detector device. When the sides of the laminations facing the primary beam are not situated in a common plane, the same formula is applicable if L is assumed to be the distance between this side and the part of the detector device which is determined by the direction of the lamination, and $L_p$ is assumed to be the distance between this part and the primary beam.

An embodiment of the device in accordance with the invention will be described in detail hereinafter with reference to the accompanying diagrammatic drawing.

Figure 1:
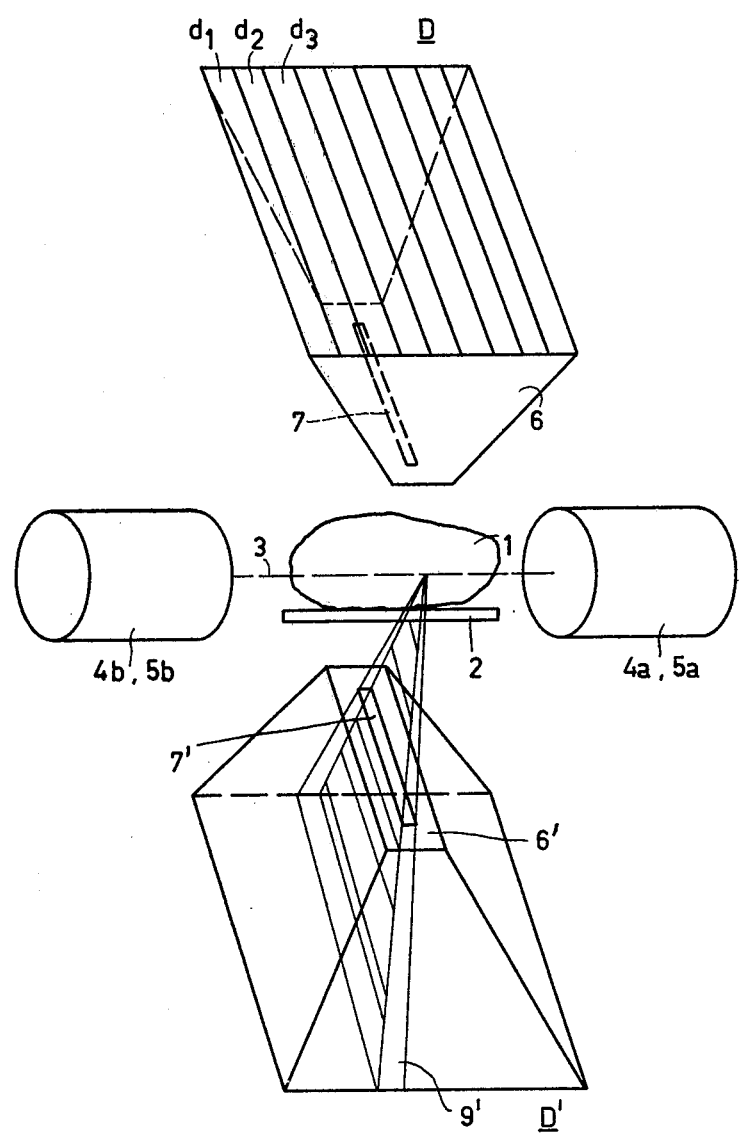
FIG. 1 shows the device for examining a body.
Figure 2:
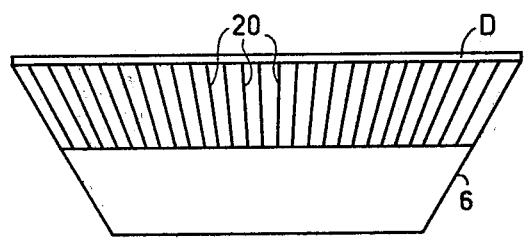
FIG. 2 shows a device comprising laminations in a flat plane extending transversely to the primary beam.
Figure 2:
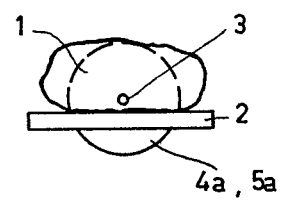

FIG. 2 shows a cross-section of the primary beam 3 which extends transverse to the plane of the drawing through a body 1 arranged on the table 2, a slit aperture 6 which is arranged, between the primary beam and a detector device D. The slit aperture 6' situated therebelow and the associated detector device D' have been omitted for the sake of clarity. The longitudinal direction of the individual detectors and of the slit extends horizontally in this figure. A large number of laminations 20 are arranged in front of the detector device D inside the slit aperture 6. The laminations are situated in flat planes which extend perpendicular to the plane of the drawing and which intersect each other in the primary beam 3. The laminations thus extend transverse to the longitudinal direction of the individual detectors and transverse to the longitudinal direction of the slit. When this geometry is used, radiation originating from a region outside the region defined by the primary beam (this kind of radiation can only be multiple scattered radiation) can no longer reach the detector device, while the scattered radiation originating from the region of the primary beam reaches the detector device after only minor attenuation, the attenuation being dependent of the ratio of lamination thickness and lamination distance.

The laminations may be combined to form an independent structural unit in the form of a scattered radiation grating, such as used in customary X-ray diagnostic apparatus. The laminations of such a scattered radiation grating must be constructed for radiation which is substantially harder than the radiation for which the laminations of a normal scattered radiation grating are constructed, because the described device utilizes radiation which is substantially harder than normally used elsewhere in X-ray diagnostics. For example, the embodiment described utilizes an X-ray source whereto a voltage of 350 kV is applied. The laminations, which may be made of lead or steel, therefore, should be longer and/or thicker than in customary scattered radiation gratings. A scattered radiation grating of this kind, however, can be manufactured in the same way as the customary scattered radiation gratings. Movement of the laminations in a plane approximately perpendicular to the beam path, analogous to the movement of the scattered radiation grating during a customary X-ray exposure, is not necessary in this case.

Optimum reduction of the scattered radiation is achieved when the distance S of the laminations on a side facing the primary beam satisfies said relation $S=wL/L_p$.

What is claimed is:

1. In a device for examining a body of the type comprising means for projecting penetrating radiation through the body in a primary beam of small cross-section area, whereby scattered radiation is produced by interaction of radiation in the primary beam with materials in the body, a plurality of radiation detectors, and slit aperture means which function to transmit the scattered radiation from the body to the detectors, the improvement comprising:

laminar radiation absorbing means, disposed between the body and the detectors, which function to transmit scattered radiation, which originates in the region of the primary beam, to the detectors and to attenuate scattered radiation, which originates outside of the primary beam and which propagates towards the detectors.

2. The improvement of claim 1 wherein the laminar radiation absorbing means comprise a plurality of laminations of a material having a high absorption factor for radiation, said laminations being spaced one from the other and disposed so that an extension of each lamination would at least approximately extend through the primary beam along the entire length of the beam.

3. The improvement claimed in claims 1 or 2 wherein the laminations are flat plates and are disposed in planes which intersect in a straight line which at least approximately coincides with the primary beam.

4. A device as claimed in claim 3 wherein ends of the laminations which are closest to the primary beam are spaced, one from the other, at a distance of approximately $S=wL/L_p$ where w is the diameter of the cross section of the primary beam, $LP_p$ is the distance between the primary beam and the detectors, and L is the distance between the ends of the laminations and the detectors.

* * * * *